(12) United States Patent
Stabacinskiene et al.

(10) Patent No.: US 8,336,405 B2
(45) Date of Patent: Dec. 25, 2012

(54) CRYOGENIC SPECIMEN HOLDER (75) Inventors: Halina Stabacinskiene, North Huntingdon, PA (US); Jeffrey J. Gronsky, Ligonier, PA (US); Christine M. Thomas, Pittsburgh, PA (US); Pushkarraj V. Deshmukh, Pittsburgh, PA (US); Alan C. Robins, Horley Surrey (GB); Paul E. Fischione, Export, PA (US)

(73) Assignee: E.A. Fischione Instruments, Inc., Export, PA (US)

( * ) Notice: Subject to any disclaimer, the term of this patent is extended or adjusted under 35 U.S.C. 154(b) by 309 days.

(21) Appl. No.: 12/845,486

(22) Filed: Jul. 28, 2010

(65) Prior Publication Data

US 2012/0024086 A1    Feb. 2, 2012

(51) Int. Cl.
*B01L 3/00*    (2006.01)
*G01N 21/00*   (2006.01)

(52) U.S. Cl. .................................. 73/864.91; 250/443.1
(58) Field of Classification Search ............... 73/864.91; 250/440.11, 441.11, 442.11, 443.1
See application file for complete search history.

(56) References Cited

U.S. PATENT DOCUMENTS

| 4,027,494 | A | | 6/1977 | Fletcher et al. | |
|---|---|---|---|---|---|
| 4,910,399 | A | | 3/1990 | Taira et al. | |
| 4,931,650 | A | * | 6/1990 | Lowe et al. | 250/397 |
| 4,950,901 | A | | 8/1990 | Jones et al. | |
| 5,235,817 | A | | 8/1993 | Gallagher et al. | |
| 5,274,237 | A | | 12/1993 | Gallagher et al. | |
| 5,302,831 | A | | 4/1994 | Gallagher et al. | |
| 5,735,129 | A | | 4/1998 | Ienaga | |
| 5,753,924 | A | * | 5/1998 | Swann | 250/443.1 |
| 5,811,816 | A | | 9/1998 | Gallagher et al. | |
| 5,821,176 | A | | 10/1998 | Yeh | |
| 5,986,270 | A | * | 11/1999 | Bormans et al. | 250/442.11 |
| 6,153,883 | A | | 11/2000 | Arai | |
| 6,388,262 | B1 | | 5/2002 | Alani et al. | |
| 6,410,925 | B1 | * | 6/2002 | Armbruster et al. | 250/442.11 |
| 7,420,184 | B2 | | 9/2008 | van de Water et al. | |
| 7,659,510 | B2 | | 2/2010 | Chao et al. | |
| 2008/0156996 | A1 | | 7/2008 | Nicolosi et al. | |

* cited by examiner

*Primary Examiner* — Hezron E Williams
*Assistant Examiner* — Nathaniel Kolb
(74) *Attorney, Agent, or Firm* — Metz Lewis Brodman Must O'Keefe LLC; Barry I. Friedman (57) ABSTRACT

An improved cryogenic specimen holder for imaging and analysis facilitates imaging at very high tilt angles with a large field of view. A retractable specimen holder tip protects the specimen during transport. An optimized Dewar design is positioned at a fixed, tilted angle with respect to the axis of the holder, providing a means of continuously cooling the specimen irrespective of the high tilt angle and the amount of liquid nitrogen present in the vessel. The Dewar neck design reduces the entrapment of nitrogen gas bubbles and its shape prevents the spilling of liquid nitrogen at high tilt angles. The specimen holder has a retractable tip that completely encapsulates the specimen within a shielded environment internal to the specimen holder body. The cooling and specimen transfer mechanisms reduce thermal drift and the detrimental effects of vibrations generated by both the evaporation of liquid nitrogen present in the Dewar as well as other environmental effects.

38 Claims, 7 Drawing Sheets

CRYOGENIC SPECIMEN HOLDER

BACKGROUND OF THE INVENTION

1. Field of the Invention

This invention relates to specimen holders for maintaining a specimen at a low temperature during visualization, imaging or analysis. More specifically it relates to holders utilized for transmission electron microscopy (TEM) and particularly to the Dewar used for the containment of liquid nitrogen and the subsequent cooling of the TEM sample placed on a retractable cartridge and positioned within a cryogenically cooled shield.

2. Description of the Prior Art

There are a variety of imaging technologies which have developed to observe and analyze specimens at the molecular and/or atomic level. These include optical, electron, x-ray and photon microscopy together with associated imaging and analysis. Cryo electron microscopy, or Cryo EM, is a powerful technique for studying frozen hydrated biological specimens in transmission electron microscopy. To generate results with minimum artifacts, specimens are rapidly frozen and then imaged in a fully hydrated state. This reduces the detrimental effects of fixatives or stains that are commonly used to prepare microscopy specimens at more ambient temperatures. Cryo EM is extremely beneficial for studying proteins, viruses, macromolecular assemblies, vesicles/liposomes, organelles, and cells in more native conditions. In order to obtain a TEM image the specimen needs to be sufficiently thin to allow for the transmission of electrons therethrough. As with all conventional TEM imaging, the TEM image is then formed by electron interactions with the specimen. The quality and usability of TEM images increases with improved resolution. Biological specimen quality is highly dependent on the method of preparation. Typical preparation includes rapidly vitrifying a thin film of suspension by freezing it in an extremely cold material, such as liquid ethane. The specimen is ultimately transferred to the TEM while being maintained in the frozen state and at a consistently low temperature and examined in its fully hydrated state. Alternatively, a bulk specimen can be cryoprotected, high pressure frozen, cryosectioned and transferred to the imaging or analytical device. The mounting/support and transfer of specimen to a TEM, as an illustrative example, for subsequent imaging has typically been performed with the help of a cryotransfer specimen holder. These prior art TEM specimen holders, consistent with TEM specimen holders, generally, comprise longitudinal rods of a given length to support and mount the specimen near one end of the rod. The rod end of the TEM specimen holder is inserted into the microscope and placed between the components of the electron optics. As is well known to those skilled in the art, these components, by physical necessity, allow for only a very small and dimensionally constrained specimen or support contained thereon. With respect to biological specimens, as indicated above, the specimen must also be maintained at a low temperature, preferably below $-140°$ C. during the transfer, imaging and analysis process and while located within the constrained space of the microscope. This is because it is desirable to maintain the ice component of the specimen in an amorphous state which exists below $-140°$ C. Above $-140°$ C., the ice will adopt a crystalline form which is detrimental to imaging and analysis. During transfer and while the specimen holder is not inserted into the imaging or analysis device, it is also essential to physically protect the specimen, as it is highly vulnerable to physical and environmental damage and/or contamination from water vapor and other sources.

The physical port of a microscope, for example, which accepts and restrains the specimen holder is known as the goniometer. It is a micromanipulator for moving the specimen holder, and thus the specimen itself, in the X, Y, Z, $\alpha$ and $\beta$ tilt directions. This helps to focus the electron beam onto the desired region of the specimen and at the precise angle/orientation necessary to observe the relevant characteristics of the specimen. As stated, the goniometer is used to tilt the specimen holder inside the column of the microscope relative to the electron imaging beam. Angular displacement of the specimen while mounted within the microscope is an extremely important feature for cryotomography in order to obtain three-dimensional, or 3D, information for life science applications. This same methodology is applicable to the physical sciences. To generate 3D information, the sample is imaged at various tilt angles and/or orientations. The two-dimensional projections are then recombined to produce a composite 3D image.

While mounted on the specimen holder, the specimen is maintained at the required low temperature through the use of a cooling medium which reduces the temperature of portions of the specimen holder and the specimen itself. This cooling medium, typically liquid nitrogen, is stored in an insulated container mounted to one end of the specimen holder, typically identified as a Dewar. The Dewar is a component of the specimen holder and it comprises a highly reflective inner vessel enclosed within an evacuated housing. The vacuum within the evacuated housing, coupled with the materials utilized for the construction of the device, thermally isolates the inner vessel from the housing. A rod or other thermal conductor assembly provides the thermal contact between the specimen and the receptacle for the cooling medium present in the Dewar. The conductor is typically constructed of a material having high thermal conductivity such as silver or copper. The cooling medium is utilized to remove the heat from the specimen support and specimen to maintain the same at the necessary low temperature.

Modern day transmission electron microscopes are capable of achieving atomic scale resolution. However, image quality and resolution are highly dependent upon reduction of specimen displacement through vibrations and drift induced from the holder during imaging or analysis. In practice, these environmental and other conditions need to be minimized to achieve optimum resolution. At atmospheric pressure, liquid nitrogen boils at $-196°$ C. In many prior art specimen holder designs, a solid conductor rod within the holder is in contact with the Dewar and the specimen support in the form of a receptacle tip. As the liquid nitrogen or other cooling medium boils off under ambient atmospheric conditions, vibrations are formed by the turbulence in the medium. The conductor rod transmits these vibrations directly to the specimen tip, causing the specimen to vibrate during imaging and analysis. The rigid contact between the Dewar and the cooling assembly of the prior art devices further introduces physical stresses on the device during thermal expansion and contraction.

Most Dewar devices are open to ambient atmosphere to permit the boil off of the liquid medium and to minimize the retention of expanding warm gas medium, which has deleterious effects relating to pressure within the vessel. The devices are rigidly constructed such that any displacement of the specimen holder results in a corresponding displacement of the specimen. In tomography, higher tilt angles of the specimen during imaging yield more accurate and detailed 3D reconstructions. The ability to increase the tilt of the specimen holder is limited, however, by the possibility of spillover of the liquid medium from the Dewar, as well as a thermal gradient induced into the walls of the container, which result in unsatisfactory results, including vibrations, drift and, potentially, spilled liquid nitrogen in the laboratory. Avoidance of this condition substantially limits the ability to tilt the specimen.

Another shortcoming of prior art cryogenic specimen holder designs is the ability to constrain thermal distortions of the device itself. Thermal variations lead to the expansion or contraction of materials. The thermal gradient present between the Dewar and the specimen cartridge, as a function of distance and time, as well as changing environmental conditions along the length of the holder, causes unpredictable and dynamic dimensional changes, resulting in specimen drift from the nominal position within the imaging device. It is desirable, therefore, to maintain the assembly at a constant, low steady state temperature with a minimum thermal gradient. Moreover, any thermal contact between the conductor assembly, which extends within, but dimensionally separate from the outer holder barrel, may introduce additional heat or, at a minimum, temperature variations within the system. In addition, since the exterior holder barrel is in contact with the microscope goniometer during imaging, any such contact between the conductor assembly and the outer holder barrel leads to an undesirable thermal path from the microscope, a large warm heat sink, and the specimen, causing additional drift.

During imaging and analysis of the specimen, constant evaporation of the cooling medium also results in a drop in the volume of liquid present in the Dewar. This necessitates the physical interface between the cooling assembly and the Dewar to be located at a point most likely to be in direct contact with the cooling medium, which is the bottom of the Dewar. At any given time, a temperature gradient exists along the wall of the Dewar, being coolest at the points of contact directly adjacent the cooling medium and increasing in temperature with increasing distance from the surface of the cooling medium. Loss of direct contact with the cooling medium immediately adjacent the interface between the cooling assembly and the Dewar causes the temperature to rise in the assembly and further exacerbates drift of the specimen during imaging.

Cryotransfer holders like those described in Swann et al., U.S. Pat. No. 5,753,924, have been developed to maintain samples at the desired temperature and to prevent frost from forming on the specimen during transfer. As illustrated in FIG. 1 of Swann, the holder 10 includes a holder body 12 and a specimen tip 14 with a source of cooling for the tip. The specimen tip 14 includes a support grid 16 of thermally conductive material and a tab portion 24 that is adapted to be secured to the specimen tip (see FIG. 5). A cryoshield is formed by an opening in the specimen holder tip 14. To load the specimen grid 16 into the tip 14 of holder body 12, tab 24 is inserted through a slot 40 in specimen tip holder 14 (see FIG. 4) which forms a cryoshield for the specimen. The specimen grid 16 is moved from an extended position to a retracted position by a drawbar 46, which is in thermal contact with support grid 16 and extends along the longitudinal axis of holder body 12.

The cryotransfer holder of Swann suffers from several disadvantages. In this design, the drawbar is in rigid thermal contact with the support grid and the holder specimen tip, thus acting as a potential source of heat load. This requires much greater energy extraction to cool the entire assembly to the desired temperature. Extraneous heat may cause thermal expansion and contraction of the cooling rod and drawbar. The rigid contact directly transfers all such movement to the specimen resulting in a loss of image resolution because of drift and vibrations. Finally, the proprietary design of the specimen grid, which requires insertion of a tab to secure the grid into the cryoholder, makes the system incompatible with any independent, standard transmission electron microscope specimen disks, which are 3 mm in diameter, or any other shapes now in use or in development.

The Dewar assembly of the type described by Gallagher et al., U.S. Pat. No. 5,302,831 has been developed in an attempt to maintain constant contact between the liquid nitrogen supply and the cold finger assembly. FIG. 2 of Gallagher illustrates a trapezoidal or truncated triangular shaped Dewar 50 with a cold finger assembly 14. A copper braided strap 122 is secured on one end through a lug 118 to the bottom wall 94 of liquid nitrogen vessel. The other end of the copper braided strap 122 is secured through a lug to a portion of the cold finger assembly 114. The triangular Dewar 50 is tapered at the bottom so that liquid nitrogen always fills the front portion of vessel 90 adjacent to the intersection of the front wall 98 and the bottom wall 94. Dewar 50 is angled so that the liquid nitrogen is forced into a portion of Dewar 50 that is in constant contact with the cold finger assembly 114 and strap 122 at a fixed angle in the range of 0° to 60°. The vessel 90 top wall 102 has an opening 103 for the addition of liquid nitrogen to Dewar 50.

The Dewar described in Gallagher is used to cool a radiation detector cold finger, which has different physical constraints than a TEM specimen holder, including, most importantly, that a specimen is not cooled thereby, merely a detector. This Dewar is not built to satisfy any of the specimen vibration and drift requirements necessary for proper TEM imaging. Also, cooling a radiation detector does not require or even permit the Dewar to be tilted about the longitudinal axis of the cold finger. Gallagher's trapezoidally shaped Dewar will not contain the liquid nitrogen at higher tilt angles, causing the liquid nitrogen to boil and spill over leading to substantial sample drift. The three corners present near the Dewar neck will also trap nitrogen gas, causing vibrations, which in turn would also limit image resolution.

There remains a need, therefore, for a cryogenic holder adapted to be rotated about the longitudinal axis of the holder, which will help tilt the specimen within the microscope while maintaining optimum thermal transmission between the liquid cooling medium and the specimen at all times. The specimen support cartridge has to be vibrationally isolated from the cooling medium and the exterior sections of the holder have to be thermally isolated from the cooling medium to provide additional reduction of sample drift and vibration and to reduce thermal stresses within the device. In addition, there is a need for a holder that includes a cartridge specimen tip that receives a standard sized specimen and optionally and controllably shields the specimen during transport to prevent contamination.

SUMMARY OF THE INVENTION

A cryogenic specimen holder is disclosed for a variety of imaging and analytical applications. The holder improves the quality of imaging and analytical information by overcoming major challenges related to holder drift and vibration. In accordance with one embodiment of the invention, a specimen holder includes a Dewar for receiving and storing a cooling medium, such as liquid nitrogen. The Dewar is constructed as a conventional vacuum flask with an interposed partial vacuum between an inner liquid support vessel and an outer protective housing. A set of flexible thermal conductors ribbons, braids or the like, including combinations thereof, are incorporated into the thermal transfer system which extracts heat from the specimen. In a preferred embodiment, one such flexible member is attached to the lowest point of the Dewar. The other end of this flexible assembly is connected to a conductor rod which is in thermal contact with the sample cartridge. A similar flexible assembly may form the thermal junction between the conductor rod and the cartridge housing. Each of the thermal ribbons, for example, in the preferred embodiment, forms a vibration damper between the various components of the cooling assembly. The inner vessel of the Dewar is preferably cylindrical and positioned at a fixed, tilted angle offset from the longitudinal axis of both the holder rotation and the exterior protective housing of the Dewar itself. This forms, in the preferred embodiment, an arcuate V-shaped bottom surface of the inner vessel which is dimensionally unchanged in orientation during tilt of the holder assembly. The flexible conductive ribbons are affixed such that they are in contact with the inner vessel at the lowest point of the arcuate bottom surface of the cylindrical shape. As a result, the cooling medium, despite reductions in volume during use, is always in contact with mounting point of the conductor ribbons to the Dewar regardless of the holder angle. Any shape or conformation, however, is acceptable which achieves this containment of the liquid cooling medium adjacent to the thermal conductor. The Dewar therefore ensures stable operating conditions at tilt angles ranging from 0° to +/−90°, and in most applications, up to +/−80°, limited only by the design of the opening in the Dewar. Additional angular displacement could therefore be possible with unique Dewar exterior shape designs which may be applicable to particular applications.

In an additional embodiment, the neck of the inner vessel is profiled such that it does not trap any nitrogen gas through the tilt range of the holder. The vessel design also prevents the liquid nitrogen from spilling over at high holder tilt angles. This provides stable, vibration free operating conditions.

The holder further may include a sample cartridge that can be retracted into a cryogenically cooled shield located within the holder tip. When in a retracted position, the thermally isolated cartridge acts as a thermal shield around the cryogenic sample and prevents sample contamination and damage. The present sample holder can therefore be successfully utilized to transfer the cryogenically prepared samples, which may be of any shape or conformation, including but not limited to, the current standard 3 mm disk, from any mounting or storage facility to an electron microscope. After insertion into the protected environment of the electron microscope, the cartridge can then be extended to the operating position for observations within the microscope. The preferred sample tip is adapted to receive and restrain standard sized and shaped samples and/or specimens, including grids, that are well known in the art.

In an additional embodiment, the retractable cartridge is spring loaded within the holder tip. This allows for the cartridge to settle in a stress free equilibrium position during the initial thermal cycling and improves thermal contact and transfer between the associated components. The spring pushes the cartridge on a pair of rollers made from insulating material that provide complete thermal isolation from the outer barrel of the holder. To provide further vibration damping the thermal contact between the cartridge and the cooling conductor rod is provided with a flexible thermally conductive ribbon assembly. The flexible ribbons also compensate for the dimensional change of the cooling rod assembly due to various thermal stress and strains.

The holder, together with its particular features and advantages, will become more apparent from the following detailed description and with reference to the appended drawings.

DESCRIPTION OF THE PREFERRED EMBODIMENTS

Figure 1:
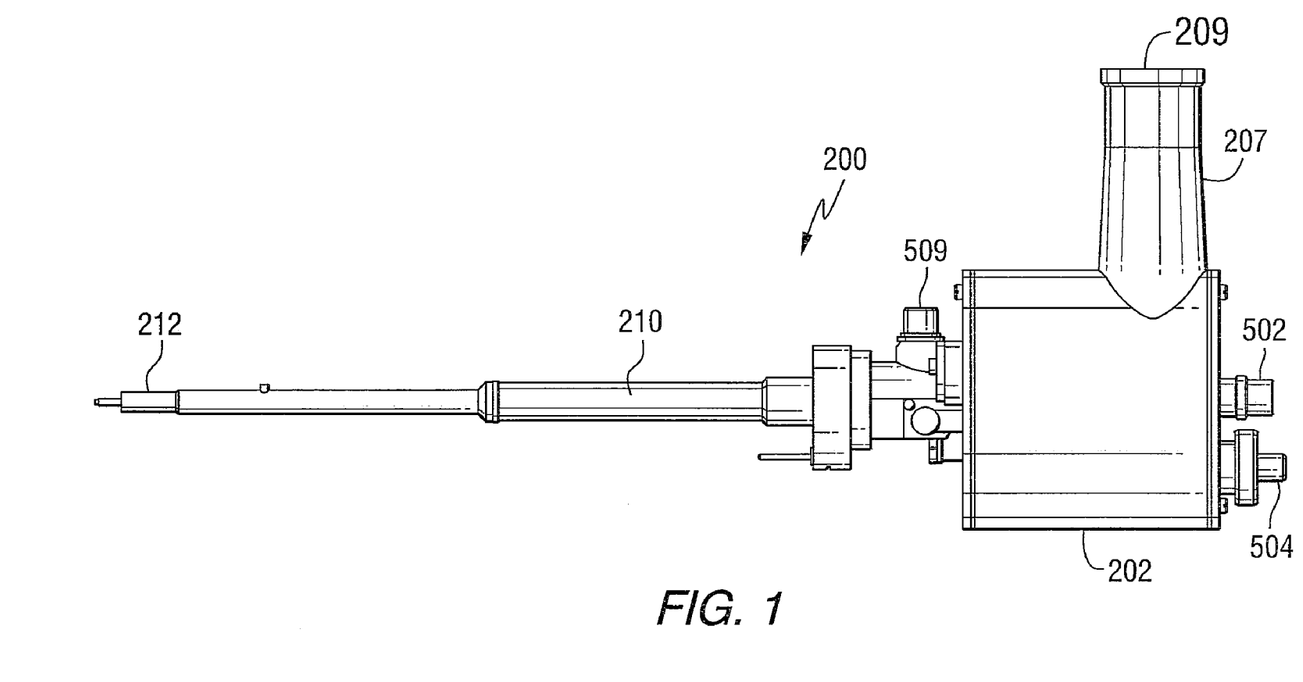
FIG. 1 is a side view of the specimen holder of the present invention.

Referring now to FIG. 1, generally, the holder 200 is comprised of three main sections. A housing 202 supports the Dewar assembly and is provided with an extension for the addition of liquid cooling medium and the escape of gas, formed by neck 207 and opening 209. A holder middle barrel 210 forms the middle section which adapted for insertion into and restraint by the goniometer, together with the front barrel 212. Further, the middle barrel 210 and front barrel 212 are designed by size and shape to place the specimen in the appropriate location within the microscope. It is to be specifically noted that the size and particular arrangement of the barrel components may vary based upon the physical constraints of microscopes manufactured by different suppliers. A front barrel 212 extends outwardly from the middle barrel 210 in a direction opposite that of the housing 202 and contains the specimen cartridge.

Figure 2:
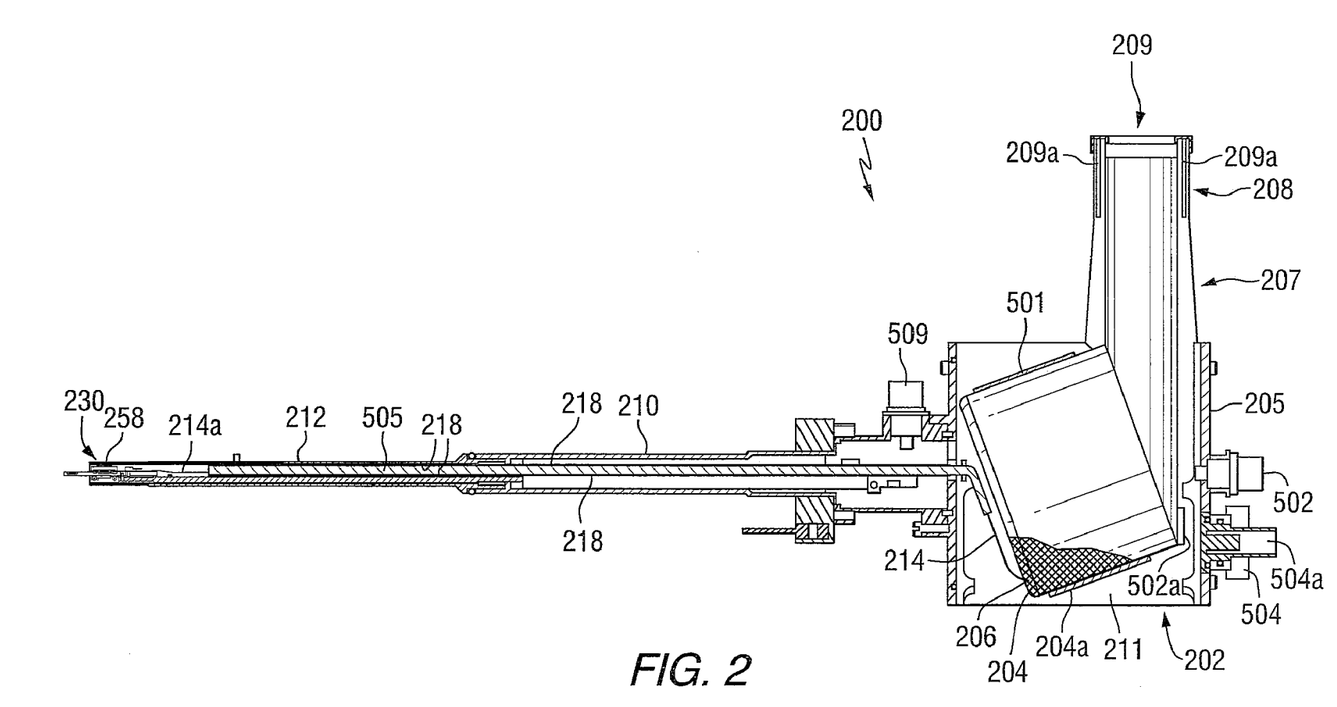
FIG. 2 is cross sectional side view of the specimen holder of the present invention.
Figure 3:
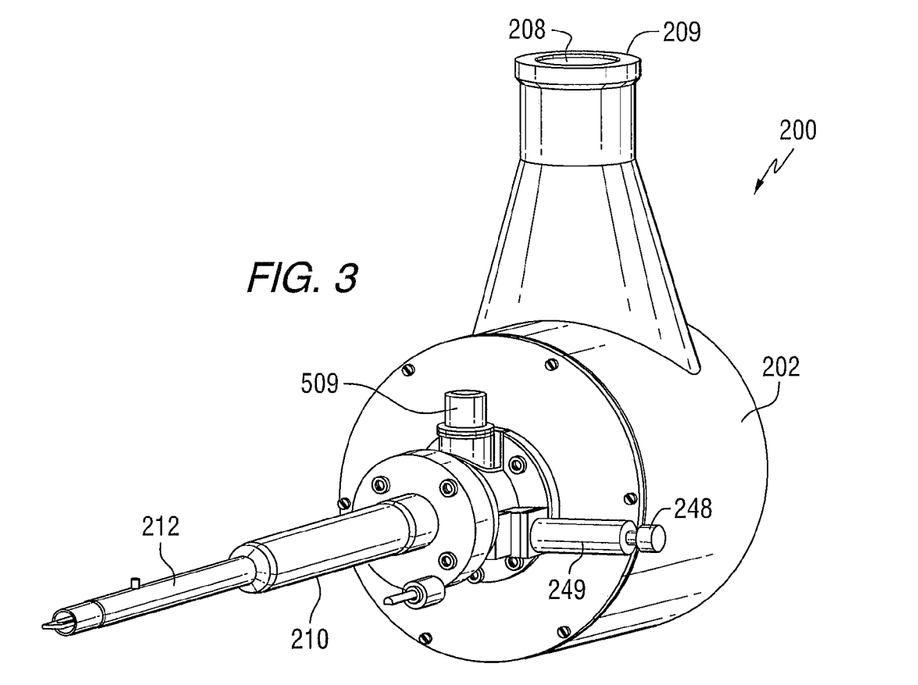
FIG. 3 is an isometric view of the specimen holder of the present invention.

Referring now to FIGS. 1 and 3, the housing 202 further comprises a valve 504 which is utilized to evacuate the insulating space within the housing 202, as will be described further with reference to FIG. 2. Electrical connectors 502, 509 are provided to permit the electrical interface between internal heating assembly 502a and internal temperature sensor 246, respectively, described more fully with reference to FIG. 2 and an external monitoring/control device (not shown). A handle assembly 249 is provided for the longitudinal displacement of the specimen holder cartridge assembly with respect to the front barrel 212, as will be described more fully with respect to FIGS. 3a and 4. The handle assembly may be constructed of any known design, including a slidably displaceable armature or through rotational knob 248 in a gear or cam system, as would be interchangeable to those skilled in the art.

Referring now to FIG. 2, the Dewar assembly is comprised of a series of component elements within housing 202. An inner vessel 204 is disposed within the housing 202 generally within an evacuated space 211. Inner vessel 204 is provided with a highly reflective outer surface to minimize the impact of any radiated heat within the housing 202. Inner vessel 204 is adapted to receive and store a liquid cooling medium, such as liquid nitrogen. The inner surface of the inner vessel 204 is highly polished, smoothed or otherwise coated to avoid surface irregularities which provide nucleation points for the formation of gas bubbles. An adsorbent or absorbent material may be mounted within inner vessel 204 to improve retention of the cooling medium at a particular location. Sponge 204a is shown as an illustrative example and may be mounted at any location within inner vessel 204a. A vacuum is created within the evacuated space 211 in order to provide thermal insulation between the cooling medium and the housing 202, as is well known to those skilled in the art. This vacuum increases stable performance by minimizing heat effects from convection of heat between the ambient atmosphere beyond the housing 202 and the cooling medium. Inner vessel 204 is supported entirely by the connection to the housing 202 located at opening 209 through reentrant tubing 208, as described more fully below. The extreme top of the inner vessel 204 and reentrant tubing 208 is sealed and secured with a glue joint 209a at the opening 209. This minimizes any physical interface and creates a long path length connection utilizing a poorly conducting material between inner vessel 204 and housing 202 which would permit thermal transfer of heat. Inner vessel 204 is surrounded with a vacuum adsorption medium 501 such as Zeolite. A heater assembly 502a is further provided within the housing 202 and affixed to inner vessel 204. Vacuum adsorption medium 501 adsorbs any moisture present within evacuated space 211. Heater assembly 502a is utilized to rapidly heat the vacuum adsorption medium 501, which produces vapor. Valve 504 selectably connects evacuated space 211 to an external vacuum system (not shown) through port 504a for evacuation purposes while being heated. This process is performed periodically, when the holder is not in use, to help optimize the vacuum conditions. Housing 202 includes additional mechanisms for securing the actuation rod 240, discussed in more detail below.

Inner vessel 204 is mounted within the housing 202 at a fixed angle with respect to the horizontal axis of the holder, for example about 20°. This angle may be in the range of 10° and 50°. The cylindrical shape of inner vessel 204, combined with its off axis mounting, allows any remaining volume of liquid nitrogen to maintain a near constant center of mass along the arcuate surface at the lowest, or other collection point of the inner vessel 204, even at high tilt angles. This applies a symmetric load distribution on the goniometer and improves the holder performance during tilting.

The housing 202 has an opening 209 for filling liquid nitrogen in the inner vessel 204. The reentrant tubing 208 connects the inner vessel 204 to the housing 202. The reentrant tubing 208 provides a long thermally insulating path, minimizing the heat gain from the housing 202 which is at ambient temperatures to the inner vessel 204 which is maintained at cryogenic temperatures. More particularly, reentrant tubing 208 is formed from a plurality of concentric cylindrical components jointed alternately at the tops and bottoms of the cylindrical components forming a sinuous support. The neck 508, as more fully illustrated with additional reference to FIG. 5, is designed to provide a smooth transition for the nitrogen gas to escape from the inner vessel 204 through the opening 209. This design ensures that inner vessel 204 does not trap any liquid nitrogen bubbles when the holder 200 is tilted to an angle of up to approximately 80°. The elimination of trapped liquid nitrogen bubbles in turn prevents vibrations, which are detrimental to image resolution. The inner vessel 204 is designed to hold approximately 200 ml of liquid nitrogen. The inner vessel design helps maintain up to 80% of the liquid nitrogen volume without spilling at the extreme tilt angles of +/−80°.

Referring again to FIG. 2, one end of a thermally conductive ribbon assembly 214 is connected to the lower arcuate section 206 of the lower circumferential surface of inner vessel 204 while the other end is connected to conductor rod 505. As a result, liquid nitrogen present in inner vessel 204 is always in proximal contact with the ribbon assembly 214, through the wall of inner vessel 204, regardless of the holder angle. The device therefore ensures stable operating conditions at high tilt angles. The flexible nature of ribbon assembly 214 further minimizes any vibrations that are generated either by the cooling medium or by any environmental conditions, such as acoustical noise. Ribbon assembly 214 also compensates for the change in length of the cooling rod assembly resulting from thermal changes and reduces the strain on the overall device.

Ribbon assembly 214 extends away from arcuate section 206 of inner vessel 204 where it is affixed to conductor rod 505 by a weld or similar joint which ensures thermal conductivity. Conductor rod 505, which may be of unitary or modular construction, extends through the body of middle barrel 210 and front barrel 212. Radiation shield 218 concentrically surrounds and seals conductor rod 505 along a substantial portion of its length, but is not in physical or thermal contact therewith, forming an evacuated space therebetween. Radiation shield 218 is constructed from a thin walled stainless steel tube or other poor thermal conductor that provides additional thermal insulation to the cold conductor rod 505. The radiation shield 218 and conductor rod 505 are mounted within, but not in physical or thermal contact with middle barrel 210 and front barrel 212. Conductor rod 505 is then connected to the specimen cartridge housing 506 at the holder tip 230 using a second ribbon assembly 214a. This ribbon assembly 214a acts similarly to ribbon assembly 214 and provides additional vibration damping between the inner vessel 204 and the specimen.

Figure 4A:
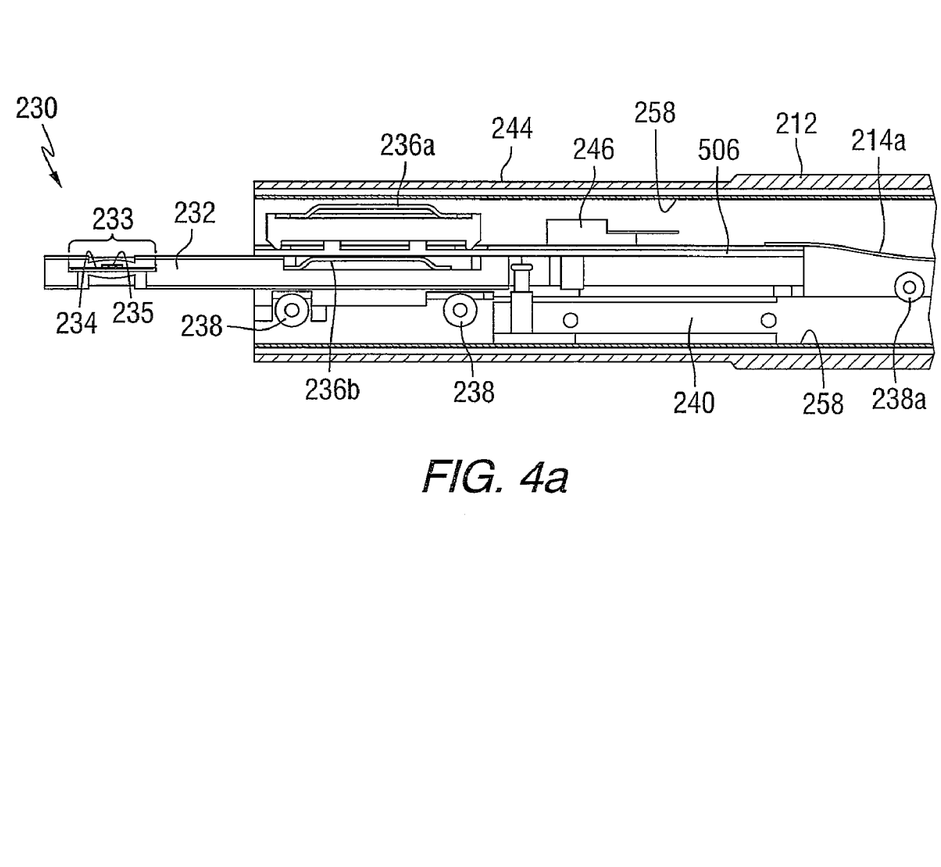
FIG. 4a is a cross sectional side view of the specimen holder tip with the sample cartridge in the extended position.
Figure 4B:
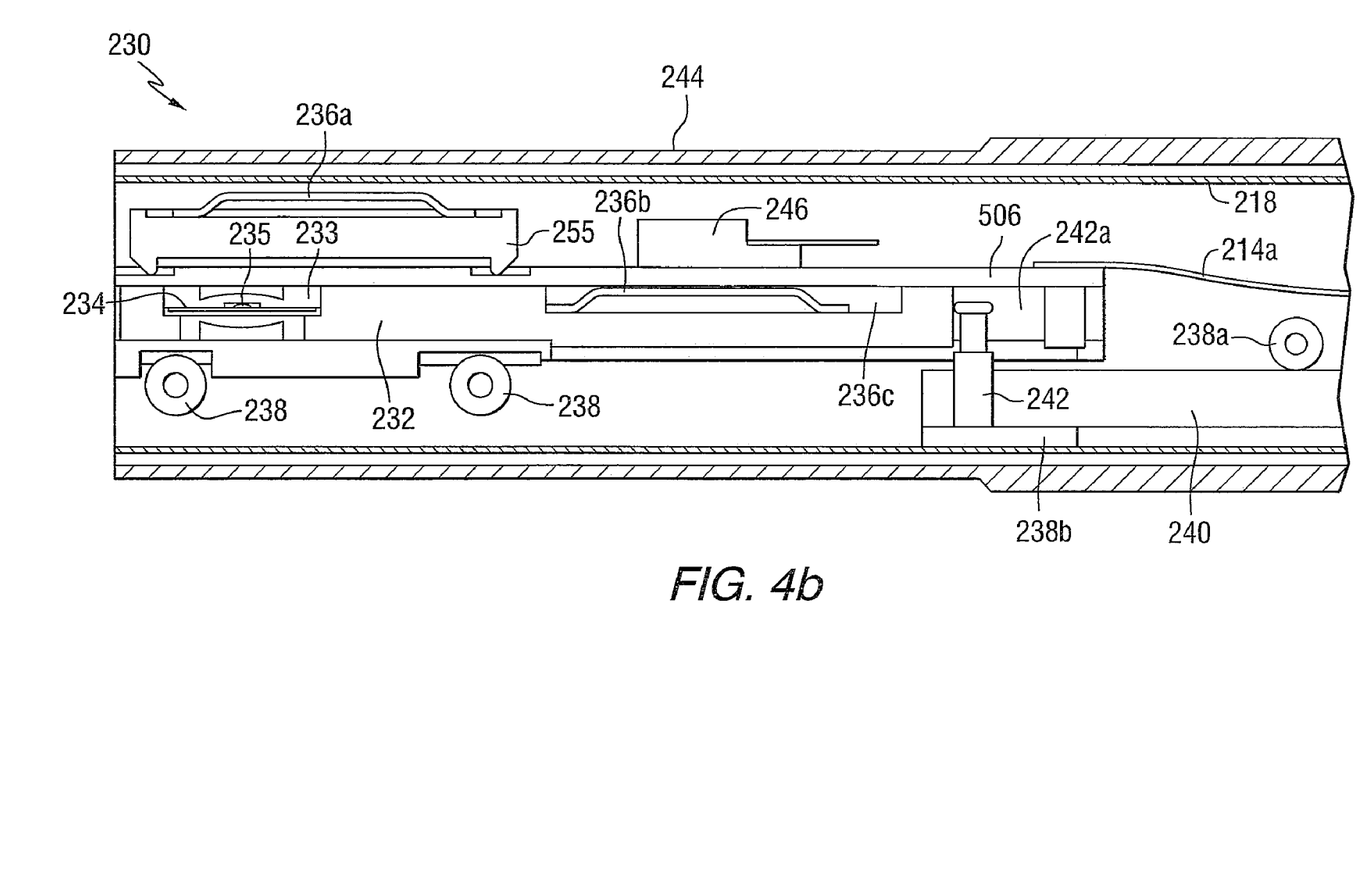
FIG. 4b is a cross sectional side view of the specimen holder tip with the sample cartridge in the retracted position.
Figure 4C:
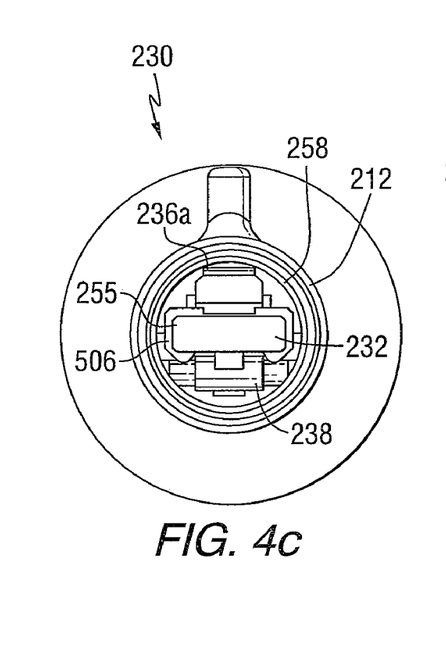
FIG. 4c is an end view of the specimen holder tip.

Referring now to FIGS. 4a, 4b and 4c, front barrel 212 is provided with an independent front insulating tube 258 which is spatially isolated from front barrel 212. Holder tip 230 includes a specimen cartridge 232 which is slidably mounted within and in good thermal contact with cartridge housing 506. Spring 236b is interposed between specimen cartridge 232 and cartridge housing 506 within spring well 236c to create a frictional interface which resists slippage therebetween, other than as specifically controlled by actuating pin 242, as will be more fully described below. Specimen cartridge 232 and cartridge housing 506 are jointly interposed between isolating mounting block 255 and isolation rods 238. Isolating mounting block 255 is itself spring loaded by spring 236a within front inner tube 258 in conjunction with isolation rods 238. Isolation rods 238 and isolating mounting block 255 jointly serve to thermally isolate cartridge housing 506 from front insulating tube 258 and the remainder of the device. Front insulating tube 258 is constructed of a poor conductor such as titanium or stainless steel to further thermally isolate specimen cartridge 232. Disposed at the distal end of specimen cartridge 232 is a recess forming specimen cup 233, which includes a supporting surface 234 for receiving and restraining specimen 235 to be viewed or imaged in a microscope system. Supporting surface 234 is adapted to receive a standard circular grid, 3 mm in diameter, or other specimen appropriate for electron microscopy or other imaging applications.

When in the forward, or operative, position as illustrated in FIG. 4a, the left lateral end of cartridge 232, and thus specimen cup 233 and specimen 235 extend outside front barrel 212. Cartridge 232 and cartridge housing 506, which are located inside front insulating tube 258 and front barrel 212, are restrained by the force of spring 236a against isolation rods 238. Springs 236a and 236b are preferably formed from a non-magnetic material such as beryllium-copper. Springs 236a and 236b are aligned such that they each exert a compressive force onto isolating mounting block 255 and specimen cartridge 232, respectively, and thus, in addition to minimizing unwanted shifts of the components, serve to dampen any stray vibrations introduced to specimen cartridge 232. In addition, springs 236a and 236b allow for specimen cartridge 232 to settle in a stress free equilibrium position during the initial thermal cycling.

Specimen cartridge 232 can be displaced in a direction parallel to a longitudinal axis of holder 200 and thus will move laterally to the left and the right as seen in the Figures. In a retracted position as illustrated in FIG. 4b, the left lateral end of specimen cartridge 232 and thus specimen cup 233, supporting surface 234 and specimen 235 reside in a position inside cartridge housing 506. Although holder tip 230 is shown in FIGS. 4a and 4b as having two springs 236a and 236b, it will be appreciated by those of skill in the art that holder tip 230 may be provided with additional springs without departing from the scope of the invention. Temperature sensor 246 is mounted directly to cartridge housing 506 to monitor the temperature of specimen 235. In order to facilitate displacement of specimen cartridge 232 relative to cartridge housing 506, actuating pin 242 is inserted within slot 242a within specimen cartridge 232. Actuating pin 242 is affixed to actuator rod 240 which extends throughout the length of the holder 200.

Figure 3A:
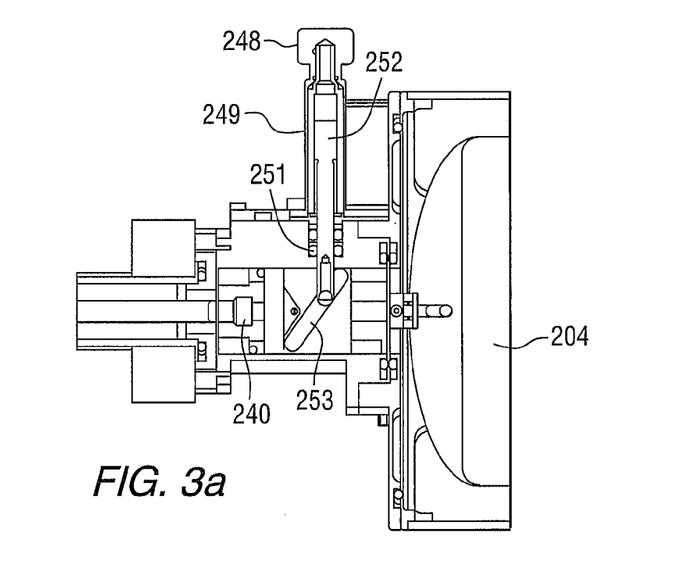
FIG. 3a is an side sectional view of the actuator assembly of the present invention.

With additional reference to FIGS. 2, 3 and 3a, handle assembly 249 is affixed to the end of actuator rod 240 proximate to the housing 202. Actuator rod 240, which may be optionally comprised of several components or modules interconnected with each other, extends within the interior space of middle barrel 210 and front barrel 212 to terminate with actuator pin 242 at the operative end of the device in order to displace specimen cartridge 232. As will be appreciated by those skilled in the art, such displacement may be in any direction or dimension. Specimen cartridge 232 is adapted for slidable displacement in a lateral direction in and out of cartridge housing 506 when a lateral force is applied to the actuator rod 240 by turning rotational knob 248. Knob 248 is affixed to actuator shaft 252 which is rotatably mounted within handle 249. O-ring seal 251 is utilized to separate the interior of the holder assembly 1, which may be under vacuum conditions, from the ambient atmosphere. It is noted that actuator shaft 252 is rotated to engage and adjust cam 253 with respect to actuator rod 240 and that the rotational motion of knob 248 causes lateral displacement of actuator rod 240 while maintaining an effective seal of O-ring 251. Actuator rod 240 is restrained in place and thermally isolated by isolation rod 238a and actuator isolation block 238b. Cam 253 and actuating rod 240 are designed such that actuating pin 242 does not physically contact the cartridge in the final extended and retracted positions of specimen cartridge 232. This eliminates a major source of heat flow, thus facilitating a more stable cartridge temperature.

Thermally conductive ribbon assembly 214 is connected to the cartridge housing 506. Ribbon assembly 214 provides a thermal conduction path from inner vessel 204, through connecting rod 505 to cartridge housing 506 and subsequently to specimen cartridge 232. As a result, the remaining holder tip 230 components, for example, actuating rod 240, actuator pin 242, spring-loaded isolating rods 238 and 238a and front barrel 212, remain at ambient temperature. Unlike the prior art references discussed previously, the ribbon assembly 214 cools only the cartridge housing 506 and in turn specimen cartridge 232. This results in an efficient cooling system. In addition, the thermal isolation of many of the holder tip 230 components greatly reduces the negative effect of thermal gradient and helps eliminate specimen drift.

Figure 5A:
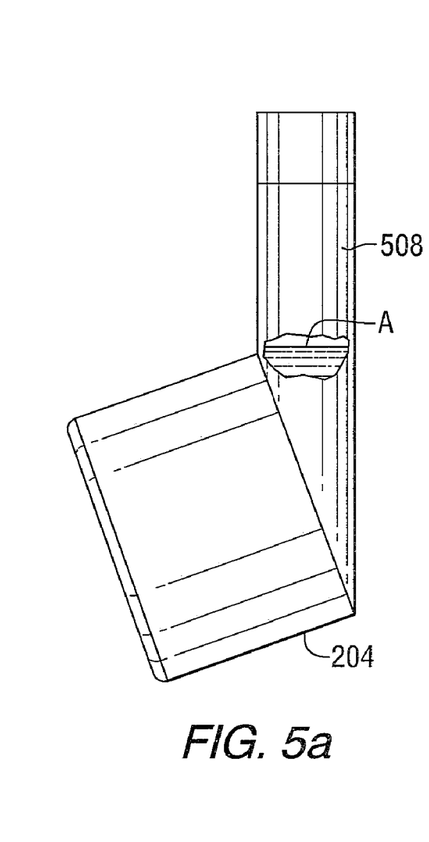
FIGS. 5a-f are various isometric views of the Dewar inner vessel containing liquid cooling medium at different tilt angles.
Figure 5B:
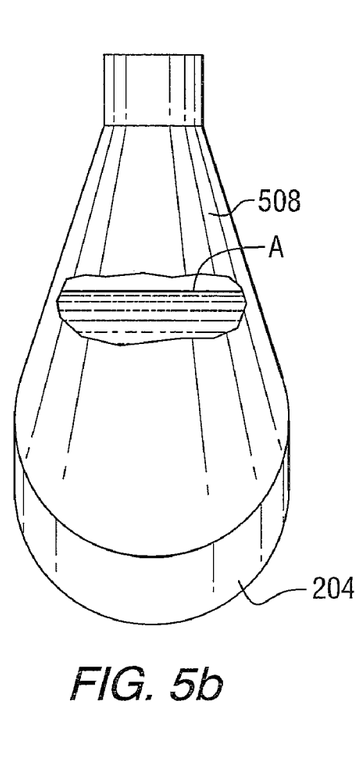
Figure 5C:
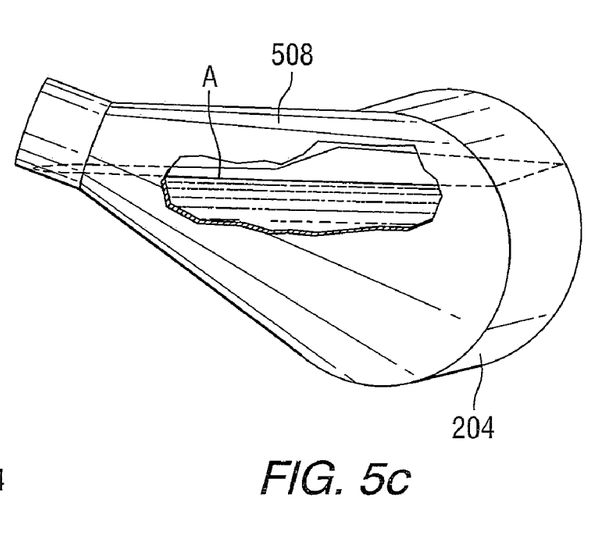
Figure 5D:
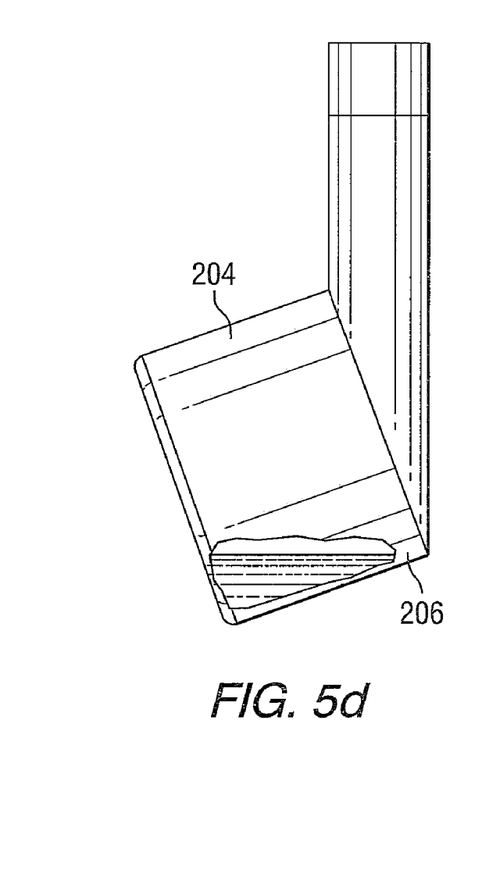
Figure 5E:
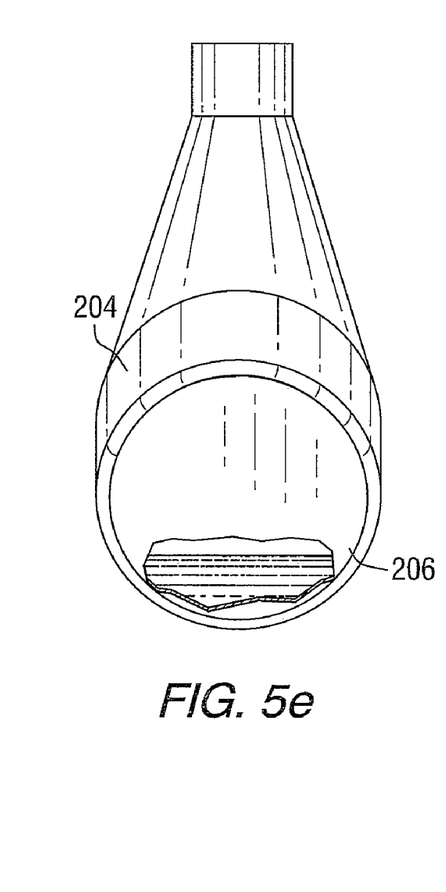
Figure 5F:
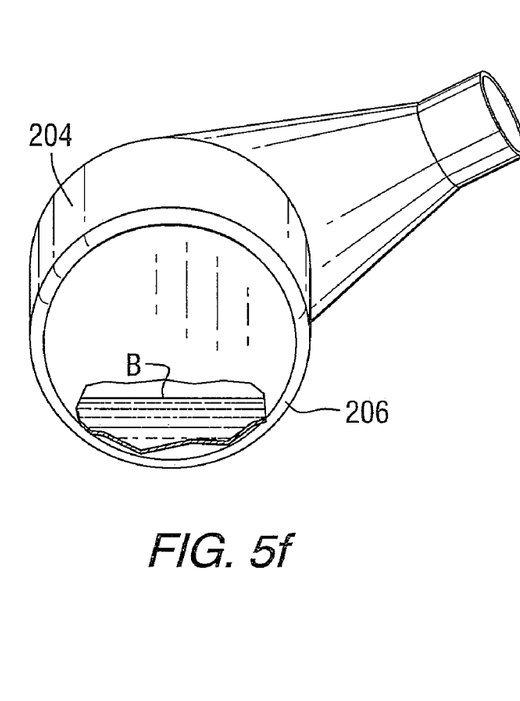

Referring now to FIGS. 5a-f, the inner vessel 204 is illustrated having varying amounts of liquid cooling medium. With respect to FIGS. 5a and 5b, inner vessel 204 is illustrated in the upright, neutral position having 0° tilt. Liquid cooling medium is filled to a level corresponding to 80% of the nominal volume of inner vessel 204, the surface of such liquid cooling medium is represented by reference A. Referring now to FIG. 5c, inner vessel 204 is illustrated at a tilt angle corresponding to the approximate limit of functionality and utility associated with the holder. The figure illustrates that even at the extreme tilt angle, the surface of the liquid cooling medium A remains within inner vessel 204 without spillage. Referring now to FIGS. 5d and 5e, inner vessel 204 is illustrated in the upright, neutral position, having 0° tilt. Liquid cooling medium is filled to a level corresponding to 10% of the nominal volume of inner vessel 204, the surface of such liquid cooling medium is represented by reference B. Lastly, FIG. 5f illustrates inner vessel 204 at the extreme tilt angle with the surface of cooling medium B at the 10% level. FIGS. 5d-f represent the likely state of inner vessel 204 after substantial use of the device and the corresponding depletion of the liquid cooling medium through boiling. The figures illustrate the substantial degree of contact between the bulk of the remaining liquid cooling medium and the lower arcuate section 206 of inner vessel 204 proximate to the thermally conductive ribbons (not shown). It is noted that at all tilt positions and at all levels of cooling medium that substantial contact is made by the cooling medium with the collection point at the lower arcuate section 206 of inner vessel 204, facilitating maximal heat transfer between the cooling medium and the thermally conductive ribbons mounted adjacent thereto.

In operation, liquid nitrogen is placed into inner vessel 204 through the opening 209. The unique design of inner vessel 204 and neck 508 help to obtain high holder tilt angles while retaining the liquid nitrogen and without trapping nitrogen gas within inner vessel 204.

The operator prepares a specimen 235 on a standard 3 mm grid in a cryogenically protected atmosphere. Other types of specimens may also benefit from this technique and can be readily position within specimen cup 233. Specimen cup 233 may also be adjusted with respect to its geometry to accommodate other shaped specimens so long as the physical constraints of the relevant imaging device are observed. Preparation and mounting of such specimens, and appropriate cryogenic chambers to perform these tasks, are well known in the art and will not be discussed at this time. The specimen 235 is then placed on supporting surface 234 of specimen cup 233 when the specimen cartridge 232 is in the forward position as illustrated in FIG. 4a. The operator then turns the knob 248 (FIG. 2) which applies lateral force to actuating rod 240. The force is transferred from actuating rod 240 to actuator pin 242, causing cartridge 232 to move in a direction laterally to and generally parallel to front barrel 212 and to the right into a retracted position as shown particularly in FIG. 4b. Specimen cartridge 232 is thus contained within cartridge housing 506. The cartridge housing 506 provides a protective and thermally cooled environment for the specimen and the holder 200 may be transported to the relevant imaging or analysis device, such as an electron microscope.

Once inside the microscope, the operator uses the knob 248 to push the actuating rod 240, thus applying lateral force to specimen cartridge 232, moving it into the appropriate position with respect to the electron optics. At the final extended position, the actuating cam 253 to disconnect the actuating pin 242 from the cartridge. The specimen may now be imaged by the electron microscope or by other imaging or analysis devices.

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions.

What is claimed is:

1. A cryogenic specimen holder which receives, cools and positions a specimen in at least one of an imaging and analytical device, said holder comprising:
an elongated housing, rotatably mountable with respect to said at least one of an imaging and analytical device plus or minus up to 90 degrees from an upright position;
a receptacle, mounted at one end of said elongated housing, receiving and supporting said specimen;
a reservoir, mounted at a second end of said elongated housing, said reservoir;
permitting storage of a liquid cooling medium; and
having a collection section, within which said liquid cooling medium is consistently located during said rotation; and
a thermal conductor affixed to said reservoir, proximate to said collection section.

2. A cryogenic specimen holder as described in claim 1, wherein said reservoir is circular in section.

3. A cryogenic specimen holder as described in claim 2, wherein said reservoir is cylindrical in shape.

4. A cryogenic specimen holder as described in claim 3, wherein said reservoir further comprises an arcuate section and said collection section is located thereon.

5. A cryogenic specimen holder as described in claim 3, wherein said cylindrical reservoir has a central axis located at its center, and the elongated housing has a longitudinal axis, said central axis of said reservoir being displaced 20 degrees from said longitudinal axis of said elongated housing.

6. A cryogenic specimen holder as described in claim 4, wherein said at least one arcuate section of said reservoir is formed by the wall of said cylindrical reservoir.

7. A cryogenic specimen holder as described in claim 1, wherein said specimen holder is adapted to be rotated about the longitudinal axis of said elongated housing causing said specimen to be displaced in a tilting manner with respect to said at least one of said imaging and analytical device.

8. A cryogenic specimen holder as described in claim 7, wherein said reservoir further comprises at least one sloped wall which receives and contains said liquid cooling medium during said rotation of said holder along said longitudinal axis.

9. A cryogenic specimen holder as described in claim 8, wherein said reservoir is cylindrical in shape and further comprises an opening for introduction of said cooling medium, said at least one sloped wall extending from a wall of said cylindrical reservoir and said opening.

10. A cryogenic specimen holder as described in claim 1, wherein said receptacle and said reservoir are thermally connected by a conductor extending within said barrel.

11. A cryogenic specimen holder as described in claim 10, wherein said thermal conductor further comprises at least one flexible member.

12. A cryogenic specimen holder as described in claim 1, wherein said reservoir is separated from said elongated housing by an evacuated space.

13. A cryogenic specimen holder as described in claim 1, wherein said reservoir is mounted within said elongated housing solely through an elongated connector which minimizes thermal conductivity between said reservoir and said elongated housing.

14. A cryogenic specimen holder as described in claim 13, wherein said elongated connector further comprises a sinuous convoluted path.

15. A cryogenic specimen holder as described in claim 1, wherein said receptacle is thermally isolated from said elongated housing.

16. A cryogenic specimen holder as described in claim 1, wherein said receptacle is slidably mounted within and thermally isolated from said elongated housing.

17. A cryogenic specimen holder as described in claim 16, wherein said slidably mounted receptacle is extended out of said elongated housing in an operative mode and retracted within said barrel in an inoperative mode.

18. A cryogenic specimen holder as described in claim 17, wherein said specimen holder is adapted to be rotated about the longitudinal axis of said elongated housing causing said specimen to be displaced in a tilting manner with respect to said at least one of an imaging and analytical devices.

19. A cryogenic specimen holder as described in claim 17, further comprising a resilient member interposed between said elongated housing and said receptacle.

20. A cryogenic specimen holder as described in claim 19, wherein said resilient member is comprised of a spring.

21. A cryogenic specimen holder as described in claim 19, wherein said receptacle is comprised of component members and said resilient member increases the force of contact between said component members of said receptacle and improves thermal transfer therebetween.

22. A cryogenic specimen holder as described in claim 17, wherein said receptacle further comprises a slidable cartridge mounted within a fixed housing.

23. A cryogenic specimen holder as described in claim 22, further comprising a resilient member interposed between said slidable cartridge and said fixed housing.

24. A cryogenic specimen holder as described in claim 23, wherein said resilient member is comprised of a spring.

25. A cryogenic specimen holder as described in claim 23, wherein said resilient member increases the force of contact between said slidable cartridge and said fixed housing and improves thermal transfer therebetween.

26. A cryogenic specimen holder as described in claim 22, said fixed housing being interposed between a plurality of isolation members which thermally and vibrationally isolate said fixed housing from said elongated housing.

27. A cryogenic specimen holder as described in claim 22, further comprising an actuator arm which is mounted within said elongated housing and is in physical contact with said slidable cartridge for the remote displacement of said slidable cartridge within said elongated housing.

28. A cryogenic specimen holder as described in claim 27, said actuator arm causing said cartridge to be extended out of said elongated housing in said operative mode and retracted within said elongated housing in said inoperative mode.

29. A cryogenic specimen holder as described in claim 27, wherein said actuator is slidably positioned within a receiving slot in said slidable cartridge.

30. A cryogenic specimen holder as described in claim 27, wherein said actuator arm is thermally and vibrationally isolated from said receptacle.

31. A cryogenic specimen holder as described in claim 30, said actuator arm further comprising a sealed rotational control which forms a barrier between a vacuum environment within said holder and ambient atmosphere.

32. A cryogenic specimen holder as described in claim 27, wherein said actuator arm further comprises a control assembly for displacement of said actuator arm.

33. A cryogenic specimen holder as described in claim 17, wherein said receptacle and said reservoir are thermally connected by a conductor extending within said elongated housing.

34. A cryogenic specimen holder as described in claim 33, wherein said thermal conductor further comprises at least one flexible member.

35. A cryogenic specimen holder as described in claim 17, further comprising a temperature sensor in thermal communication with said receptacle.

36. A cryogenic specimen holder as described in claim 17, wherein said receptacle is thermally isolated from said elongated housing.

37. A cryogenic specimen holder as described in claim 17, wherein said reservoir further comprises one of an adsorbent and absorbent material to retain said liquid cooling medium at a particular point therein.

38. A cryogenic specimen holder as described in claim 1, wherein said reservoir further comprises one of an adsorbent and absorbent material to retain said liquid cooling medium at a particular point therein.

* * * * *